US00PP34710P2

(12) United States Plant Patent
Yam

(10) Patent No.: US PP34,710 P2
(45) Date of Patent: Nov. 1, 2022

(54) ***CALATHEA* PLANT NAMED 'STELLA'**

(50) Latin Name: *Calathea leitzei*
Varietal Denomination: 'STELLA'

(71) Applicant: Tai Yam, Apopka, FL (US)

(72) Inventor: Tai Yam, Apopka, FL (US)

( * ) Notice: Subject to any disclaimer, the term of this patent is extended or adjusted under 35 U.S.C. 154(b) by 0 days.

(21) Appl. No.: 17/732,970

(22) Filed: Apr. 29, 2022

(51) Int. Cl.
*A01H 5/12* (2018.01)
*A01H 6/00* (2018.01)

(52) U.S. Cl.
USPC ..... Plt./375
CPC ..... *A01H 6/00* (2018.05)

(58) Field of Classification Search
USPC ..... Plt./375
CPC ..... A01H 5/12
See application file for complete search history.

(56) References Cited

PUBLICATIONS https://shopee.co.id/Tanaman-hias-calathea-fiona-i.290212809.3881971740; May 17, 2022; 2 pages.*

* cited by examiner

*Primary Examiner* — Kent L Bell
(74) *Attorney, Agent, or Firm* — Cassandra Bright

(57) ABSTRACT

A new and distinct *Calathea* cultivar named 'STELLA' is disclosed, which develops a showy plant with consistent white, green, and light green marble variegation throughout the entire leaves as well as darker green margins and a translucent purple color on the underside of the leaf surface. Plants are compact and well-suited for 4-inch and 6-inch commercial pots. Foliage is strong with wavy leaf margins and an over somewhat undulating leaf aspect. The new variety is a *Calathea*, typically produced as an indoor ornamental plant.

2 Drawing Sheets

Figure 1:
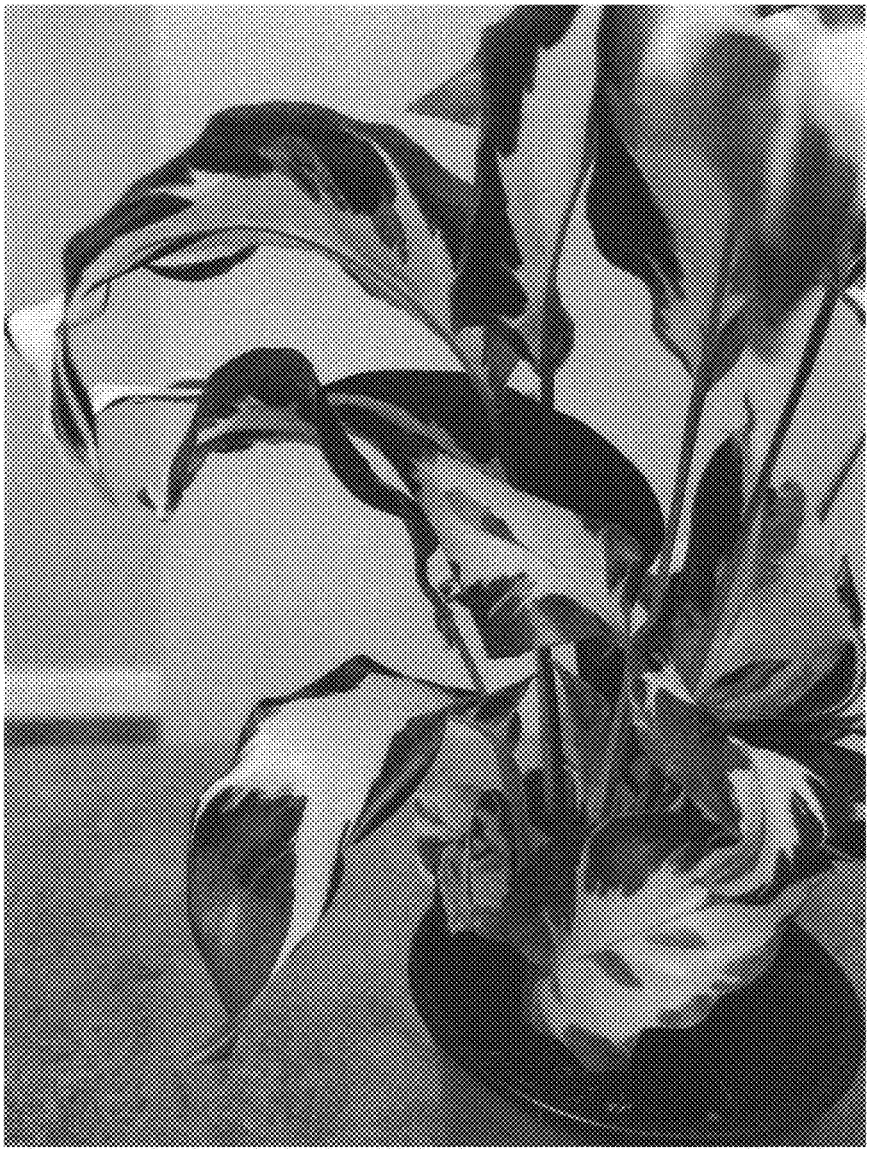

Latin name of the genus and species: *Calathea leitzei.*
Variety denomination: 'STELLA'.

BACKGROUND OF THE INVENTION

The new cultivar is a product of chance discovery by the inventor Tai Yam. The new variety 'Stella' was discovered as a naturally occurring, whole plant at a commercial nursery in Malaysia during October of 2021. The interesting mutation was identified in a commercial planting of *Calathea lietzei* 'Fusion White', U.S. Plant Pat. No. 26,187.

Asexual reproduction of the new cultivar 'STELLA' was first performed at a commercial nursery in Malaysia by vegetative cuttings in October of 2021. Plants were tested and evaluated to determine the stability of the variegation. During the propagation testing period, plants showed consistent stability of the interesting variegation. Subsequently the inventor confidentially tested the variegation for stability as finished plants at his nursery in Apopka, Fla. Production of finished plants has also shown that the unique features of this cultivar are stable and reproduced true to type.

SUMMARY OF THE INVENTION

The cultivar 'STELLA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'STELLA'. These characteristics in combination distinguish 'STELLA' as a new and distinct *Calathea* cultivar:

1. Showy plant with consistent white, green, and light green marble variegation throughout the entire leaves as well as darker green margins and a translucent purple color on the underside of the leaf surface.
2. Purple translucent color during the early stage of the leaves on the lower leaf surface.
3. Strong foliage.
4. Undulating, wavy leaf margins.
5. Undulating leaf aspect.
6. Compact growth habit, well-suited for 4-inch and 6-inch commercial pots.

PARENT COMPARISON

Plants of the new cultivar 'STELLA' are similar to the parent *Calathea lietzei* 'Fusion White' in most horticultural characteristics. The new variety however differs in the following characteristics:

1. *Calathea* 'Stella' lower surface of leaves shows more dark purple translucent color during the early stage of the leaves and some on the mature lower leaf surface.
3. *Calathea* 'Stella' has a stronger leaf lamina than *Calathea* 'Fusion White'.
4. *Calathea* 'Stella' has wavier leaf margins than *Calathea* 'Fusion White'.
5. *Calathea* 'Stella' is a taller plant than *Calathea* 'Fusion White'.
6. *Calathea* 'Stella' grows quicker and has a more tolerant response to higher light levels than 'Fusion White'.

COMMERCIAL COMPARISON

'STELLA' can be compared to the unpatented commercial variety *Calathea* 'Freddie'. Plants of 'Freddie' are similar to plants of 'STELLA' in most horticultural characteristics. However 'STELLA' differs from 'Freddie' in the following characteristics:

1. 'STELLA' is a less upright plant than 'Freddie'.
2. 'STELLA' has foliage variegation of various shades of green and white, whereas plants of 'Freddie' have foliage variegation which is green and dark green.
3. 'STELLA' plants produce foliage variegation which varies considerably among the different leaves, whereas plants of 'Freddie' produce the same variegation pattern on every leaf.
4. Plants of 'STELLA' produce side shoots vigorously from and early age, whereas plants of 'Freddie' produce side shoots on a limited basis.

'STELLA' can be compared to the patented commercial variety *Calathea rosea picta* 'Dottie', U.S. Plant Pat. No. 12,736. Plants of *Calathea* 'Dottie' are similar to plants of 'STELLA' in most horticultural characteristics. However, 'STELLA' differs from *Calathea* 'Dottie' in the following characteristics:

1. Plants of 'STELLA' have less tolerance for high light levels than plants of 'Dottie'.
2. 'STELLA' has foliage variegation of various shades of green and white, whereas plants of 'Dottie' have foliage variegation which is dark green and pink.
3. 'STELLA' plants produce foliage variegation which varies considerably among the different leaves, whereas plants of 'Dottie' produce the same variegation pattern on almost every leaf.

BRIEF DESCRIPTION OF THE PHOTOGRAPHS

The accompanying photograph in FIG. 1 illustrates in full color a typical plant of 'STELLA' grown in a greenhouse in Apopka, Fla. This plant is approximately 4 months old, shown in a 4 inch pot.

Figure 2:
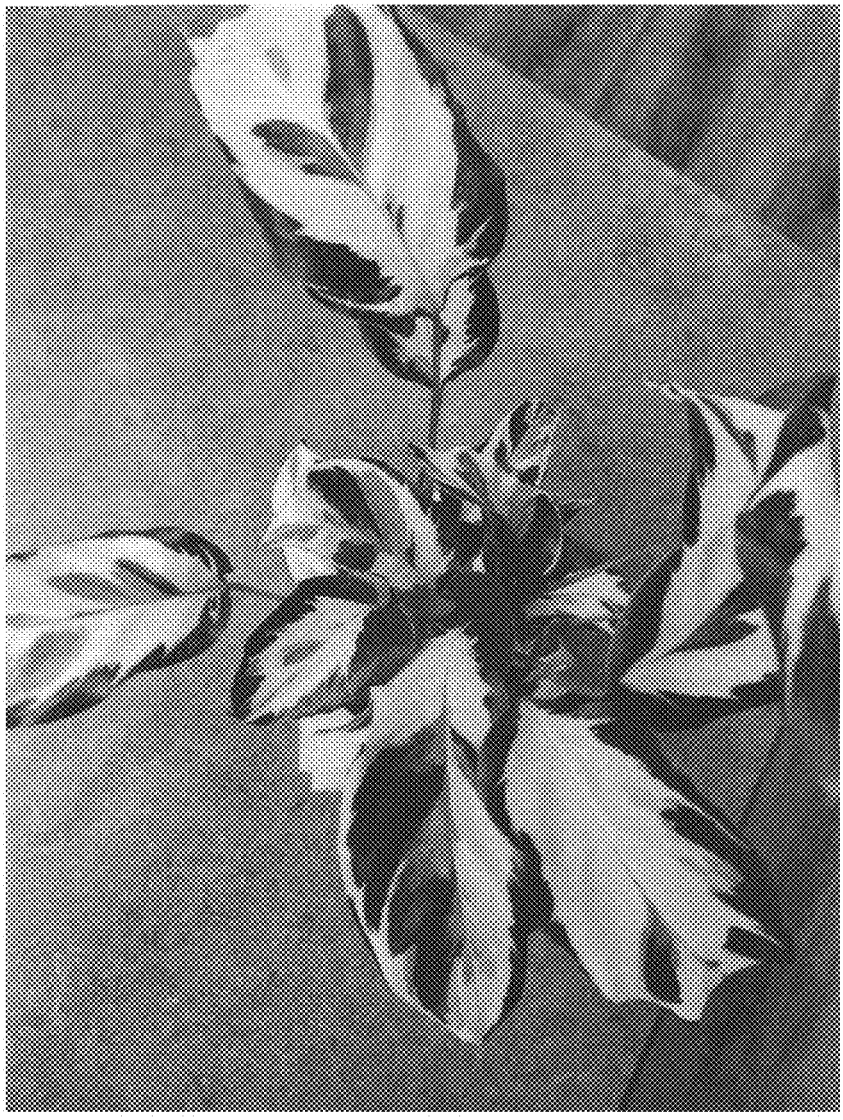

FIG. 2 illustrates a top view of the same plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'STELLA' plants grown in a polyhouse in Apopka, Fla., USA. Temperatures ranged from 80° F. to 90° F. during the day, 65° F. to 70° F. at night. No artificial light, photoperiodic treatments were given to the plants. For the first 2 months, plants were grown in shade, resulting in approximately 350 to 550 foot candles of light. After 2 months, the heavy shade is removed, and plants are finished at a natural light condition which varies between 550 to 10,000 foot candles. Measurements and numerical values represent averages of typical plant types.

Botanical classification: *Calathea leitzei* 'STELLA'.

Age of plant described: 120 days from a rooted cutting.

PROPAGATION AND PRODUCTION

Time to initiate roots: Summer: 30 to 40 days at approximately 85° F. Winter: 40 to 50 days at approximately 64° F.

Root description: Roots emerge from nodes in rhizomes. Roots approximately 3 mm thick, colored near RHS White 155A. Rhizomes Green-White 157A, irregular oblong, approximate diameter range from 5 mm to 1.3 cm. Length varies with age, typically 1.0 cm to 3.0 cm.

Time to produce a finished plant: From cuttings to a 72 cell pack takes approximately 4 weeks to finish a 4-inch saleable pot. About 8 to 10 months to finish a 6-inch pot, which will be about 18 to 20 inches tall. The variance in time depends upon the time of year.

PLANT

Growth habit: Compact, growth. Basal leaves emerge in clumps.

Pot size of plant described: 4 inch.

Plant vigor: Slightly less than moderate, as typical with strongly variegated plants.

Plant shape: Upright, slightly outwardly arching, forming an irregular oval.

Height: 12 inches.

Plant spread: 7 inches.

Main stem color: Near RHS Yellow-Green 145C.

Main stem texture: Smooth.

Main stem length: Average range 5.5 inches.

Main stem diameter: Average approximately 2.5 cm.

Main stem strength: Flexible, easily resists breaking.

Branching characteristics: No true branching. New leaves emerge direct from base of plant.

Number of clumps of leaves: 4 to 6 clumps.

Number of leaves per clump: Average 6 to 8.

Age of plant described: 120 days from a rooted cutting.

Internodes: Not present. Individual stems arise from the rhizomes. No branching.

FOLIAGE

Leaf:

*Arrangement.*—Single leaves emerging basally, in clumping rosettes. No leaf internode.

*Quantity per stem.*—2 to 3.

*Average length.*—4 to 6 inches.

*Average width.*—1.5 inches.

*Shape of blade.*—Somewhat broad elliptic.

*Aspect.*—Undulating. Somewhat curling appearance.

*Apex.*—Acute.

*Base.*—Rounded

*Margin.*—Entire, undulating, and wavy.

*Appearance.*—Semi-glossy upper and lower surfaces.

*Texture of top surface.*—Smooth.

*Texture of bottom surface.*—Smooth.

*Color.*—Immature foliage upper side: Near RHS Green 137A, 139A, 138C, Greyed-Green 193B, and White 155A. All colors present individually in large, irregular patches and marbled variegations. Margin near Green 137A and 139A. Immature foliage under side: Near RHS Purple N79C completely overlaying variegation of Green 139A, 138C and White 155A. Mature foliage upper side: Near RHS Green 137A, 139A, 138C, Greyed-Green 193B, and White 155A. All colors present individually in large, irregular patches and marbled variegations. Margin near Green 137A and 139A. Mature foliage under side: Variegation of Green 139A, 138C and White 155A. Some overlay of Purple N78B.

Venation:

*Type*.—Pinnate.

*Venation coloration upper side*.—Indistinguishable from leaf blade coloration.

*Venation coloration under side*.—Indistinguishable from leaf blade coloration.

*Petiole*.—Length: 6 inches. Diameter: Approximately 2 mm. Color: Near RHS Yellow-Green 145B lightly flushed Purple N78C. Texture: Smooth.

*Petiole sheath*.—Length: Approximately 1 to 1.5 inches. Diameter: Approximately 0.8 inches. Color: Near RHS Yellow-Green 145C and White 155A. Texture: Smooth.

FLOWERS

Not observed to date and not typically producing flowers.

OTHER CHARACTERISTICS

Disease and pest resistance: Typical resistance and susceptibility to normal pests and diseases of *Calathea* has been observed. Typical diseases found in the Marantaceae family include: *Pseudomonas species, Pseudomonas cichorii, Alternaria alternata, Fusarium oxysporum*. Typical pests include: *Radopholus similis, Tetranychus urticae*, and various flies from the Sciaridae family.

Drought tolerance and cold tolerance: The new cultivar is a typical *Calathea*, cold tolerant to approximately 55° F. and does not tolerate drought. High temperature tolerance to at least 90° F.

Fruit/seed production: Not observed.

What is claimed is:

1. A new and distinct cultivar of *Calathea* plant named 'STELLA' as herein illustrated and described.

* * * * *